United States Patent
Seo et al.

(10) Patent No.: US 11,305,649 B2
(45) Date of Patent: Apr. 19, 2022

(54) APPARATUS AND METHOD FOR CONTROLLING ALCOHOL INTERLOCK

(71) Applicants: Hyundai Motor Company, Seoul (KR); Kia Motors Corporation, Seoul (KR)

(72) Inventors: Sang Kyung Seo, Seoul (KR); Eung Hwan Kim, Seoul (KR); Gyun Ha Kim, Incheon (KR); Dae Yun An, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 200 days.

(21) Appl. No.: 16/801,985

(22) Filed: Feb. 26, 2020

(65) Prior Publication Data

US 2021/0101482 A1    Apr. 8, 2021

(30) Foreign Application Priority Data

Oct. 8, 2019   (KR) .................. 10-2019-0124726

(51) Int. Cl.
| | |
|---|---|
| B60K 28/06 | (2006.01) |
| H04N 5/33 | (2006.01) |
| B60K 28/12 | (2006.01) |
| B60R 22/48 | (2006.01) |
| A61B 5/00 | (2006.01) |
| A61B 5/18 | (2006.01) |

(Continued)

(52) U.S. Cl.
CPC .......... B60K 28/063 (2013.01); A61B 5/0077 (2013.01); A61B 5/015 (2013.01);
(Continued)

(58) Field of Classification Search
CPC ...... B60K 28/063; B60K 28/12; B60K 28/06; A61B 5/0077; A61B 5/015; A61B 5/082; A61B 5/18; A61B 5/4845; A61B 5/6893; B60R 22/48; B60R 2022/4816; B60R 2022/4891; G01N 1/2226; G01N 33/98; G01N 2001/2244; G01N 33/48; G01N 2021/8578; G06K 9/00845; G06K 9/00228; G06K 9/00288; H04N 5/33; B60W 40/08;
(Continued)

(56) References Cited

U.S. PATENT DOCUMENTS

| | | | | |
|---|---|---|---|---|
| 3,815,087 A | * | 6/1974 | Hirano ................. | B60K 28/063 180/272 |
| 2008/0154535 A1 | * | 6/2008 | Sparks ............... | G05B 19/0425 702/130 |

(Continued)

*Primary Examiner* — Ryan W Sherwin
(74) *Attorney, Agent, or Firm* — Mintz Levin Cohn Ferris Glovsky and Popeo, P.C.; Peter F. Corless (57) ABSTRACT

An apparatus for controlling alcohol interlock includes a sensor that senses an environment of a driver's seat and a camera that obtains a face image of a passenger and an image of exhalation of the passenger. A controller activates a start lock mode of a vehicle and determines whether a condition for detecting components of the exhalation of the passenger is satisfied based on the environment of the driver's seat. The controller determines whether the exhalation of the passenger is exhalation of a driver based on the face image of the passenger and the image of the exhalation of the passenger, and determines whether to detect alcohol concentration in the exhalation of the passenger based on the determination result.

20 Claims, 6 Drawing Sheets

(51) Int. Cl.
*A61B 5/08* (2006.01)
*A61B 5/01* (2006.01)
*G01N 1/22* (2006.01)
*G01N 33/98* (2006.01)
*G06V 20/59* (2022.01)

(52) U.S. Cl.
CPC .............. *A61B 5/082* (2013.01); *A61B 5/18* (2013.01); *A61B 5/4845* (2013.01); *A61B 5/6893* (2013.01); *B60K 28/12* (2013.01); *B60R 22/48* (2013.01); *G01N 1/2226* (2013.01); *G01N 33/98* (2013.01); *G06V 20/597* (2022.01); *H04N 5/33* (2013.01); *B60R 2022/4816* (2013.01); *B60R 2022/4891* (2013.01); *G01N 2001/2244* (2013.01)

(58) Field of Classification Search
CPC ............. B60W 30/1884; B60W 50/08; B60W 2040/0836; B60W 2420/42
See application file for complete search history.

(56) References Cited

U.S. PATENT DOCUMENTS

| | | | |
|---|---|---|---|
| 2009/0164069 A1* | 6/2009 | Yanagisawa | B60K 28/063 701/45 |
| 2013/0021153 A1* | 1/2013 | Keays | G01N 33/497 340/539.12 |
| 2013/0066223 A1* | 3/2013 | Beck | G01N 33/497 600/532 |
| 2015/0204844 A1* | 7/2015 | Nothacker | G06K 9/00288 73/23.3 |
| 2016/0081587 A1* | 3/2016 | Ghazarian | A61B 5/11 600/301 |
| 2017/0132521 A1* | 5/2017 | Xu | B60W 40/08 |
| 2017/0274768 A1* | 9/2017 | Hok | B60K 28/063 |
| 2018/0074081 A1* | 3/2018 | Wakana | H04N 5/23206 |
| 2018/0116579 A1* | 5/2018 | Omi | B60W 40/08 |
| 2020/0101982 A1* | 4/2020 | Bowers | B60K 28/04 |
| 2020/0122731 A1* | 4/2020 | Vanhelle | B60K 28/063 |

* cited by examiner

APPARATUS AND METHOD FOR CONTROLLING ALCOHOL INTERLOCK

CROSS-REFERENCE TO RELATED APPLICATION

This application claims the benefit of priority to Korean Patent Application No. 10-2019-0124726, filed on Oct. 8, 2019, the entire contents of which are incorporated herein by reference.

TECHNICAL FIELD

The present disclosure relates to an apparatus and a method for controlling alcohol interlock, and more particularly, to an apparatus and method for controlling alcohol interlock that prevent abnormal measurement of a driver or surrogate measurement of a fellow passenger.

BACKGROUND

Occurrence of traffic accidents due to driving under the influence is increasing, and in response thereto, laws and enforcement thereof are being strengthened to prevent the accidents related to driving under the influence. Despite such countermeasures, it is difficult to prevent the driving under the influence. Thus, recently, an alcohol interlock apparatus that measures blood alcohol concentration of a driver in a vehicle and prevents driving of the vehicle when alcohol is detected has been developed.

However, when the measurement of the driver's blood alcohol concentration is difficult to obtain due to abnormal measurement of the driver or surrogate measurement of a fellow passenger, accurate measurement of the driver's own blood alcohol concentration is difficult. Thus, there are limitations in prevention of the driving under the influence.

SUMMARY

The present disclosure provides an apparatus and method for controlling alcohol interlock that prevent abnormal measurement of a driver or surrogate measurement of a fellow passenger, so that driver's own blood alcohol concentration may be measured more accurately.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, an apparatus for controlling alcohol interlock may include a sensor configured to sense an environment or state of a driver's seat, a camera configured to obtain a face image of a passenger and an image of exhalation of the passenger, and a controller configured to activate a start lock mode of a vehicle and determine whether a condition for detecting components of the exhalation of the passenger is satisfied based on the environment or state of the driver's seat, determine whether the exhalation of the passenger is exhalation of a driver based on the face image of the passenger and the image of the exhalation of the passenger, and determine whether to detect alcohol concentration in the exhalation of the passenger based on the determination result.

In one exemplary embodiment, the controller may be configured to determine whether a door at the driver's seat is opened, whether a window at the driver's seat is opened, and whether a seat belt at the driver's seat is fastened based on the environment or state of the driver's seat, and determine whether the condition for detecting the components of the exhalation is satisfied based on the determination result. Additionally, the controller may be configured to determine that the condition for detecting the components of the exhalation is satisfied in response to determining that the door is closed, the window is closed, and the seat belt of the driver's seat is fastened. The camera may include a thermal imaging camera configured to detect thermal images of a passenger's face and the exhalation of the passenger.

The controller may be configured to determine the number of face images detected based on the thermal image, detect the image of the exhalation of the passenger based on the thermal image to determine a direction of air movement by the exhalation of the passenger, detect a position of the passenger's face based on the thermal image to determine whether the number of face images in a predetermined area including the driver's seat exceeds one, and determine whether the exhalation of the passenger is exhalation of the driver based on the determination result. In addition, the controller may be configured to determine the exhalation of the passenger as the exhalation of the driver when although the number of face images detected based on the thermal image exceeds one, the direction of the air movement is not directed from a passenger's seat to the driver's seat, and the number of face images in the predetermined area including the driver's seat does not exceed one.

The controller may be configured to determine the exhalation of the passenger as the exhalation of the driver when the number of face images detected based on the thermal image is one. In addition, the controller may be configured to determine the number of detected face images, a direction of the passenger's face, and a degree of mouth opening based on the face image of the passenger, and determine whether the exhalation of the passenger is the exhalation of the driver based on the determination result. In response to determining that the exhalation of the passenger is the exhalation of the driver, the controller may be configured to determine whether to detect the alcohol concentration in the exhalation of the passenger detected as the exhalation of the driver. The controller may be configured to release the start lock mode when the alcohol concentration does not exceed a reference value.

According to another aspect of the present disclosure, a method for controlling alcohol interlock may include sensing an environment of a driver's seat, obtaining a face image of a passenger and an image of exhalation of the passenger, activating a start lock mode of a vehicle and determining whether a condition for detecting components of the exhalation of the passenger is satisfied based on the environment or state of the driver's seat, determining whether the exhalation of the passenger is exhalation of a driver based on the face image of the passenger and the image of the exhalation of the passenger, and determining whether to detect alcohol concentration in the exhalation of the passenger based on the determination result.

In one exemplary embodiment, the determining of whether the condition for detecting the components of the exhalation of the passenger is satisfied may include determining whether a door at the driver's seat is opened, whether a window at the driver's seat is opened, and whether a seat belt of the driver's seat is fastened based on the environment or state of the driver's seat, and determining whether the condition for detecting the components of the exhalation is satisfied based on the determination result. In addition, the determining of whether the condition for detecting the components of the exhalation of the passenger is satisfied may include determining that the condition for detecting the components of the exhalation is satisfied in response to determining that the door is closed, the window is closed, and the seat belt of the driver's seat is fastened.

The obtaining of the face image of the passenger and the image of the exhalation of the passenger may include obtaining thermal images of a passenger's face and the exhalation of the passenger. The determining of whether the exhalation of the passenger is the exhalation of the driver may include determining the number of face images detected based on the thermal image, detecting the image of the exhalation of the passenger based on the thermal image to determine a direction of air movement by the exhalation of the passenger, detecting a position of the passenger's face based on the thermal image to determine whether the number of face images in a predetermined area including the driver's seat exceeds one, and determining whether the exhalation of the passenger is exhalation of the driver based on the determination result.

Further, the determining of whether the exhalation of the passenger is the exhalation of the driver may include determining the exhalation of the passenger as the exhalation of the driver when although the number of face images detected based on the thermal image exceeds one, the direction of the air movement is not directed from a passenger's seat to the driver's seat, and the number of face images in the predetermined area including the driver's seat does not exceed one. The determining of whether the exhalation of the passenger is the exhalation of the driver may include determining the exhalation of the passenger as the exhalation of the driver when the number of face images detected based on the thermal image is one.

In one exemplary embodiment, the determining of whether the exhalation of the passenger is the exhalation of the driver may include determining the number of detected face images, a direction of the passenger's face, and a degree of mouth opening based on the face image of the passenger, and determining whether the exhalation of the passenger is the exhalation of the driver based on the determination result. In addition, the determining of whether to detect the alcohol concentration in the exhalation of the passenger based on the determination result may include when the exhalation of the passenger is determined as the exhalation of the driver, determining whether to detect the alcohol concentration in the exhalation of the passenger detected as the exhalation of the driver. The method may further include releasing the start lock mode when the alcohol concentration does not exceed a reference value.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present disclosure may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the exemplary embodiment of the present disclosure, a detailed description of the related known configuration or function will be omitted when it is determined that it interferes with the understanding of the embodiment of the present disclosure.

In describing the components of the exemplary embodiment according to the present disclosure, terms such as first, second, A, B, (a), (b), and the like may be used. These terms are merely intended to distinguish the components from other components, and the terms do not limit the nature, order or sequence of the components. Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
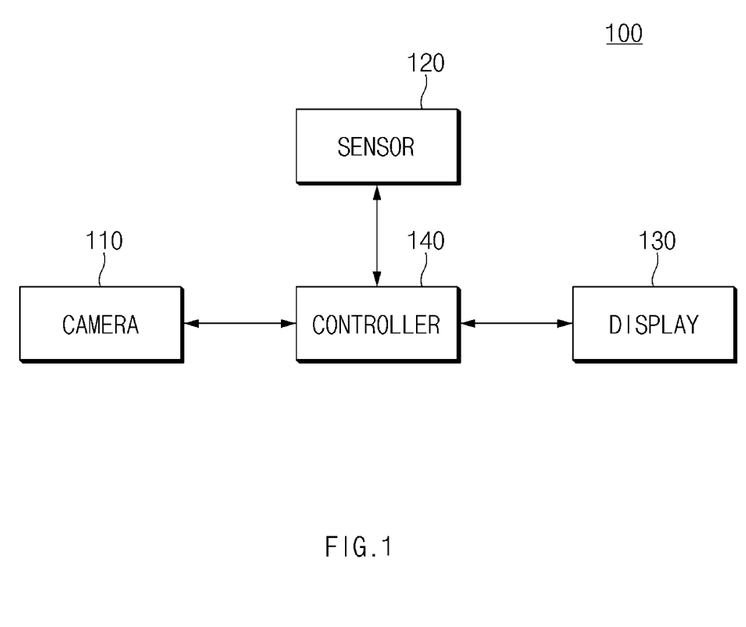
FIG. 1 is a view illustrating a configuration of an alcohol interlock controlling apparatus according to an exemplary embodiment of the present disclosure.

FIG. 1 is a view illustrating a configuration of an alcohol interlock controlling apparatus according to an exemplary embodiment of the present disclosure. As shown in FIG. 1, an alcohol interlock controlling apparatus 100 according to an exemplary embodiment of the present disclosure may include a camera 110, a sensor 120, a display 130, and a controller 140. The controller 140 may be configured to operate the other components of the apparatus.

The camera 110 may be configured to obtain a face image of a passenger. Accordingly, the camera 110 may include an internal camera configured to obtain a vehicle interior image. The camera 110 may be disposed on a center fascia, a steering wheel, a cluster, or the like to obtain the face image of the passenger. The camera 110 may include a CCD camera including a charge-coupled device (CCD) image sensor or a CMOS camera including a CMOS color image sensor. In this connection, the CCD and the CMOS both refer to a sensor configured to convert light received through a lens of the camera 110 into an electrical signal and store the electrical signal.

In addition, the camera 110 may be configured to obtain the face image of the passenger and an exhalation image of the passenger as a thermal image. The exhalation image of the passenger may include an image of air emitted from a mouth of the passenger. In general, air emitted from a mouth may be distinguished from air in an atmosphere due to a temperature difference. The camera 110 may include an infrared camera having an infrared sensor and a thermal imaging camera having a thermal sensor to obtain the image of the air emitted from the mouth.

The sensor 120 may be configured to detect an environment or state of a driver's seat. In particular, the sensor 120 may be configured to detect an opening/closing state of a door at the driver's seat, an opening/closing state of a window at a driver's seat, and whether a seat belt of the driver's seat is fastened. Accordingly, the sensor 120 may include a door sensor, a window sensor, and a seat belt sensor. In addition, the sensor 120 may be configured to detect blood alcohol concentration included in exhalation of the passenger. The sensor 120 may include an alcohol sensor. The alcohol sensor may be disposed at a position capable of detecting exhalation of the driver, that is, around a steering wheel or a cluster.

When a detection condition of components of the passenger's exhalation is not satisfied or in response to determining that the exhalation of the passenger is not the exhalation of the driver based on determination of the controller 140, the display 130 may be configured to output a message providing a notification. The display 130 may include a cluster and an audio video navigation (AVN), and may be implemented as a display device adopting a liquid crystal display (LCD) panel, a light emitting diode (LED) panel, an organic light emitting diode (OLED) panel, a plasma display panel (PDP), or the like. The liquid crystal display may include a thin film transistor liquid crystal display (TFT-LCD, Thin Film Transistor-LCD).

The controller 140 may be implemented by various processing devices such as a microprocessor embedding a semiconductor chip capable of calculating or executing various commands. Further, the controller 140 may be configured to execute overall operations of the alcohol interlock controlling apparatus according to an exemplary embodiment of the present disclosure. Specifically, the controller 140 may be configured to activate a start lock mode and determine whether the condition for detecting the components of the exhalation of the passenger is satisfied based on an environment of the driver's seat, determine whether the exhalation of the passenger is the exhalation of the driver based on the face image of the passenger and the exhalation image of the passenger, and determine whether to determine the alcohol concentration in the exhalation of the passenger based on the determination result.

Additionally, the controller 140 may be configured to determine whether the door at the driver's seat is opened, whether the window at the driver's seat is opened, and whether the seat belt of the driver's seat is fastened based on the environment of the driver's seat detected by the sensor 120, and determine whether the condition for detecting the exhalation component of the passenger is satisfied based on the determination result. The determining of whether the condition for detecting the components of the exhalation of the passenger is satisfied may include determining whether there is a factor that prevents the detection of the alcohol concentration in the exhalation of the passenger when the sensor 120 detects the alcohol concentration in the exhalation of the passenger. Further, the determining of whether the condition for detecting the components of the exhalation of the passenger is satisfied may include determining whether the passenger is sitting on the driver's seat and executing actual driving.

In response to determining that the door at the driver's seat is closed, the window at the driver's seat is closed, and the seat belt of the driver's seat is fastened, the controller 140 may be configured to determine that the condition for detecting the components of the exhalation of the passenger is satisfied. In other words, when the door and the window at the driver's seat are closed to block inflow of air from the outside, to allow the alcohol concentration in the exhalation of the passenger to be detected more easily, and when the seat belt of the driver's seat is fastened thus allowing to determine that the passenger is seated on the driver's seat, the controller 140 may be configured to determine that the condition for detecting the components of the exhalation of the passenger is satisfied. On the other hand, in response to determining that the door at the driver's seat is open, the window at the driver's seat is open, or the seat belt of the driver's seat is not fastened, the controller 140 may be configured to determine that the condition for detecting the components of the exhalation of the passenger is not satisfied.

In other words, when the door and the window at the driver's seat are opened thus allowing the inflow of the air from the outside, and causing difficult in detecting the alcohol concentration in the exhalation of the passenger, and when the seat belt of the driver's seat is not fastened, allowing the passenger to be determined not to be seated on the driver's seat, the controller 140 may be configured to determine that the condition for detecting the components of the exhalation of the passenger is not satisfied. In addition, in response to determining that the condition for detecting the components of the exhalation of the passenger is not satisfied, the controller 140 may be configured to operate the display 130 to output a message to provide a notification regard the state. According to the exemplary embodiment, the controller 140 may be configured to output a message of a 'request to close the door/window and fasten the seat belt of the driver's seat' through the display 130.

In response to determining that the condition for detecting the components of the exhalation of the passenger is satisfied, the controller 140 may be configured to determine whether the exhalation of the passenger is the exhalation of the driver. According to the exemplary embodiment, the controller 140 may be configured to determine the number of detected face images based on the thermal image of the face image of the passenger obtained from the camera 110, determine a direction of air movement in an image of the exhalation of the passenger based on the thermal image of the image of the exhalation of the passenger, and determine whether the exhalation of the passenger is the driver's exhalation based on the determination result.

Specifically, the controller 140 may be configured to determine whether the number of face images in the thermal image is one based on the thermal image. When the number of face images in the thermal image is greater than one, the controller 140 may be configured to determine that there are more than one face images in the thermal image. The controller 140 may be configured to detect the image of the exhalation of the passenger based on the thermal image to determine the direction of the air movement of the exhalation of the passenger, detect a position of a passenger's face based on the thermal image to determine whether the number of face images in a predetermined area including the driver's seat exceeds one, and determine whether the exhalation of the passenger is the exhalation of the driver based on the determination result.

When the direction of the air movement is not directed from a passenger's seat to the driver's seat, and the number of face images in the predetermined area including the driver's seat does not exceed one, the controller 140 may be configured to determine the exhalation of the passenger as the exhalation of the driver. In other words, when the number of face images in the predetermined area including the driver's seat does not exceed one, the controller 140 may be configured to determine that only the passenger in the driver's seat is detected. Further, since the direction of the air movement is not directed from the passenger's seat to the driver's seat, the exhalation of the passenger in the driver's seat may be determined as the exhalation of the driver.

On the other hand, when the direction of the air movement is directed from the passenger's seat to the driver's seat, and when the number of face images in the predetermined area including the driver's seat exceeds one, the controller 140 is unable to determine that the exhalation of the passenger is the exhalation of the driver. In other words, when the number of face images in the predetermined area including the driver's seat exceeds one, the controller 140 may be configured to determine that a passenger is detected in addition to a driver in the driver's seat in an area adjacent to the driver's seat, and may not determine the exhalation of the passenger as the exhalation of the driver since the direction of the air movement is directed from the passenger's seat to the driver's seat.

Further, when the number of face images is one as the determination result of whether the number of face images in the thermal image is one, the controller 140 may be configured to determine that a face image of the passenger is not detected. In other words, when the number of face images in the thermal image is one, the controller 140 may be configured to determine the passenger seated in the driver's seat as the driver, and thus determine the exhalation of the passenger as the exhalation of the driver. The controller 140 may additionally be configured to determine whether a difference between a passenger's body temperature and a typical body temperature exceeds a predetermined temperature based on the thermal image to assign a weight for determining a state of the passenger as an intoxicated state. When the difference between the passenger's body temperature and the typical body temperature exceeds the predetermined temperature, the controller 140 may be configured to determine that the passenger's state is likely to be the intoxicated state by assigning the weight.

In addition, according to another exemplary embodiment of the present disclosure, the controller 140 may be configured to determine the number of face images detected, a direction of the face of the passenger, and a degree of opening of the mouth based on the face image of the passenger obtained from the camera 110, and determine whether the passenger is the driver based on the determination result. More specifically, the controller 140 may be configured to determine whether the number of face images in the image is one based on the image obtained from the CCD camera or the CMOS camera.

When the number of face images in the image is greater than one, the controller 140 may be configured to determine that there are more than one face images. In particular, the controller 140 may be configured to detect the face direction and the mouth opening degree of the passenger based on the image to determine whether the face direction and the mouth opening degree of the passenger are similar to those of the exhalation of the passenger, detect the position of the passenger's face based on the image to determine whether the number of face images in the predetermined area including the driver's seat exceeds one, and determine whether the exhalation of the passenger is the exhalation of the driver based on the determination result. In addition, the determining of whether the face direction and mouth opening degree of the passenger are similar to those of the exhalation of the passenger may be understood as determining whether the passenger's face is directed from the passenger's seat to the position where the sensor 120 is disposed and whether the degree of mouth opening is similar to a degree of mouth opening during the exhalation.

When the face direction and the mouth opening degree of the passenger are not similar to those of the exhalation of the passenger, and when the number of face images in the predetermined area including the driver's seat does not exceed one, the controller 140 may be configured to determine the exhalation of the passenger as the exhalation of the driver. In other words, when the number of face images in the predetermined area including the driver's seat does not exceed one, the controller 140 may be configured to determine that only the passenger in the driver's seat is detected. Further, since the face direction of the passenger is not directed to the position where the sensor 120 is disposed from the passenger's seat, the controller 140 may be configured to determine that the exhalation of the passenger as the exhalation of the driver.

On the other hand, when the face direction and the mouth opening degree of the passenger are similar to those of the exhalation of the fellow passenger, and when the number of face images in the predetermined area including the driver's seat exceeds one, the controller 140 may not be configured to determine that the exhalation of the passenger is the exhalation of the driver. In other words, when the number of face images in the predetermined area including the driver's seat exceeds one, the controller 140 may be configured to determine that the passenger is detected in addition to the driver on the driver's seat in the area adjacent to the driver's seat. Since the face direction of the passenger is directed from the passenger's seat to the position where the sensor 120 is disposed, the controller 140 is configured to not determine the exhalation of the passenger as the exhalation of the driver. In other words, the controller 140 is unable to determine that the exhalation of the passenger is the exhalation of the driver.

When the number of face images is one as the determination result of whether the number of face images in the thermal image is one, the controller 140 may be configured to determine that the face image of the fellow passenger is not detected. In other words, when the number of face images in the image is one, the controller 140 may be configured to determine the passenger seated on the driver's seat as the driver, and thus determine the exhalation of the passenger as the exhalation of the driver.

When the exhalation of the passenger is determined as the exhalation of the driver, the controller 140 may be configured to determine to detect the alcohol concentration in the exhalation of the passenger determined as the exhalation of the driver. In particular, the controller 140 may be configured to detect the alcohol concentration only for the exhalation of the passenger in the driver's seat. In response to determining that the exhalation of the passenger is not the exhalation of the driver on the driver's seat, the controller 140 may be configured to output a message requesting retry of an exhalation operation through the display 130 to measure the exhalation of the passenger.

The controller 140 may be configured to release a start lock function of the vehicle when the alcohol concentration detected in the exhalation of the passenger is less than a reference value, and to redetect the alcohol concentration in the exhalation of the passenger when the alcohol concentration detected in the exhalation of the passenger is equal to or greater than the reference value. In addition, the controller 140 may be configured to start the vehicle when the start lock mode is released.

Figure 2:
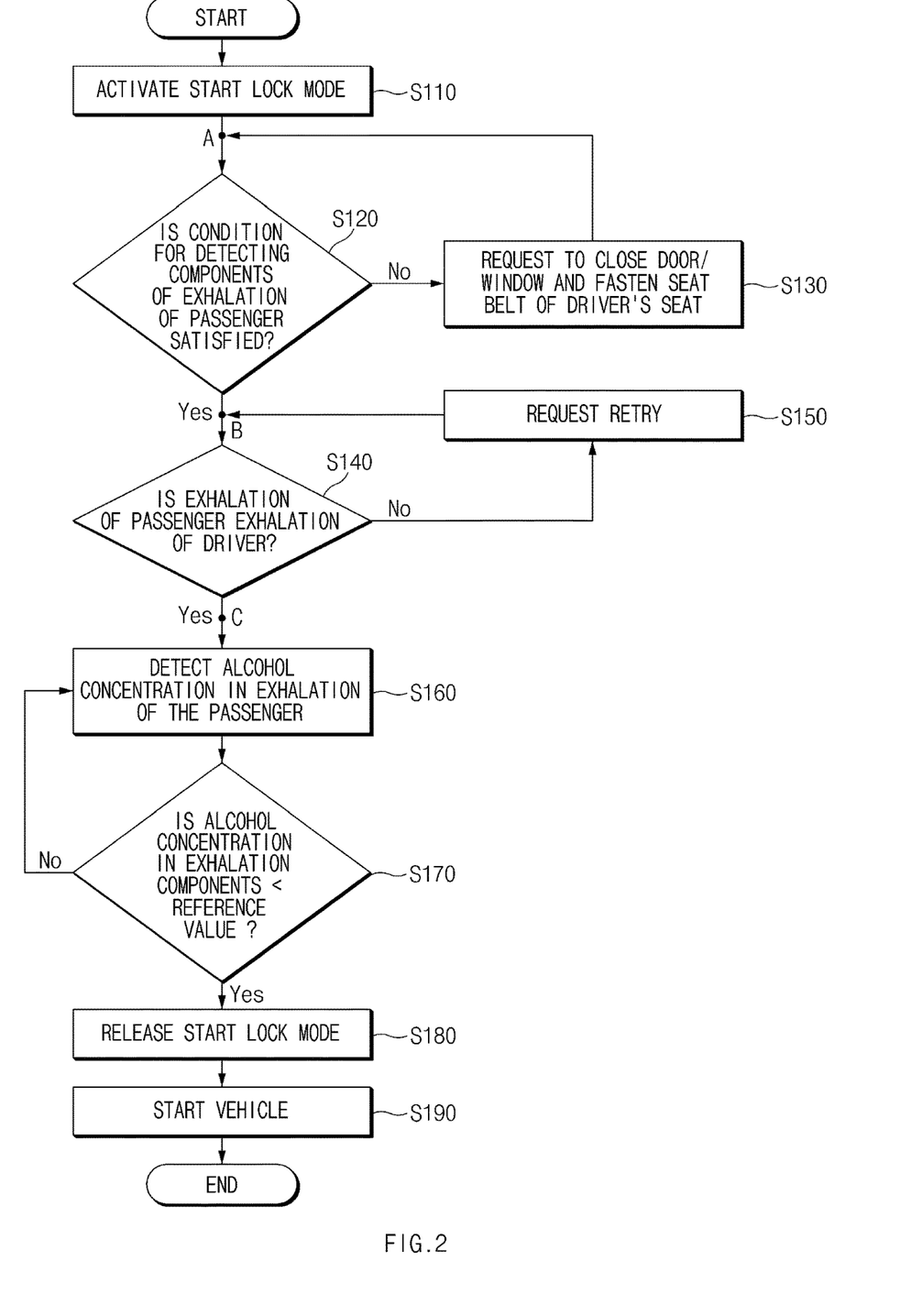
FIG. 2 is a flowchart illustrating an alcohol interlock controlling method according to an exemplary embodiment of the present disclosure.

FIG. 2 is a flowchart illustrating an alcohol interlock controlling method according to an exemplary embodiment of the present disclosure. As shown in FIG. 2, the controller 140 may be configured to activate the start lock mode (S110). In S110, the controller 140 may be configured to activate the start lock mode to fundamentally block driving of the vehicle in the intoxicated state, to prevent the passenger from arbitrarily starting the vehicle. When the start lock mode is activated, the controller 140 may be configured to determine whether the condition for detecting the components of the exhalation of the passenger is satisfied (S120). The S120 process will be described in more detail with reference to FIG. 3.

In response to determining in S120 that the condition for detecting the components of the exhalation of the passenger is not satisfied (N), the controller 140 may be configured to output a message providing a notification that the condition for detecting the components of the exhalation of the passenger is not satisfied through the display 130 (S130). According to the exemplary embodiment, in S130, the controller 140 may be configured to output the message such as 'request to close the door/window and fasten the seat belt of the driver's seat' through the display 130.

Further, in response to determining that the condition for detecting the components of the exhalation of the passenger is satisfied (Y), the controller 140 may be configured to determine whether the exhalation component of the passenger is the exhalation of the driver (S140). The process in S140 will be described in more detail with reference to FIG. 4. In response to determining in S140 that the exhalation of the passenger is the exhalation of the driver (Y), the controller 140 may be configured to detect the alcohol concentration in the exhalation of the passenger determined as the exhalation of the driver (S160). In S160, the controller 140 may be configured to detect the alcohol concentration only for the exhalation of the passenger at the driver's seat. On the other hand, in response to determining in S140 that the exhalation of the passenger is not the exhalation of the driver (N), the controller 140 may be configured to output a message requesting a retry of the exhalation operation through the display 130 to measure the exhalation of the passenger (S150).

When the alcohol concentration in the exhalation of the passenger detected in S160 is less than the reference value (Y), the controller 140 may be configured to release the start lock function of the vehicle (S180). When the alcohol concentration in the exhalation of the passenger is equal to or greater than the reference value, the controller 140 may be configured to redetect the alcohol concentration in the exhalation of the passenger (S160). In addition, in S180, when the start lock mode is released, the controller 140 may be configured to start the vehicle (S190).

Figure 3:
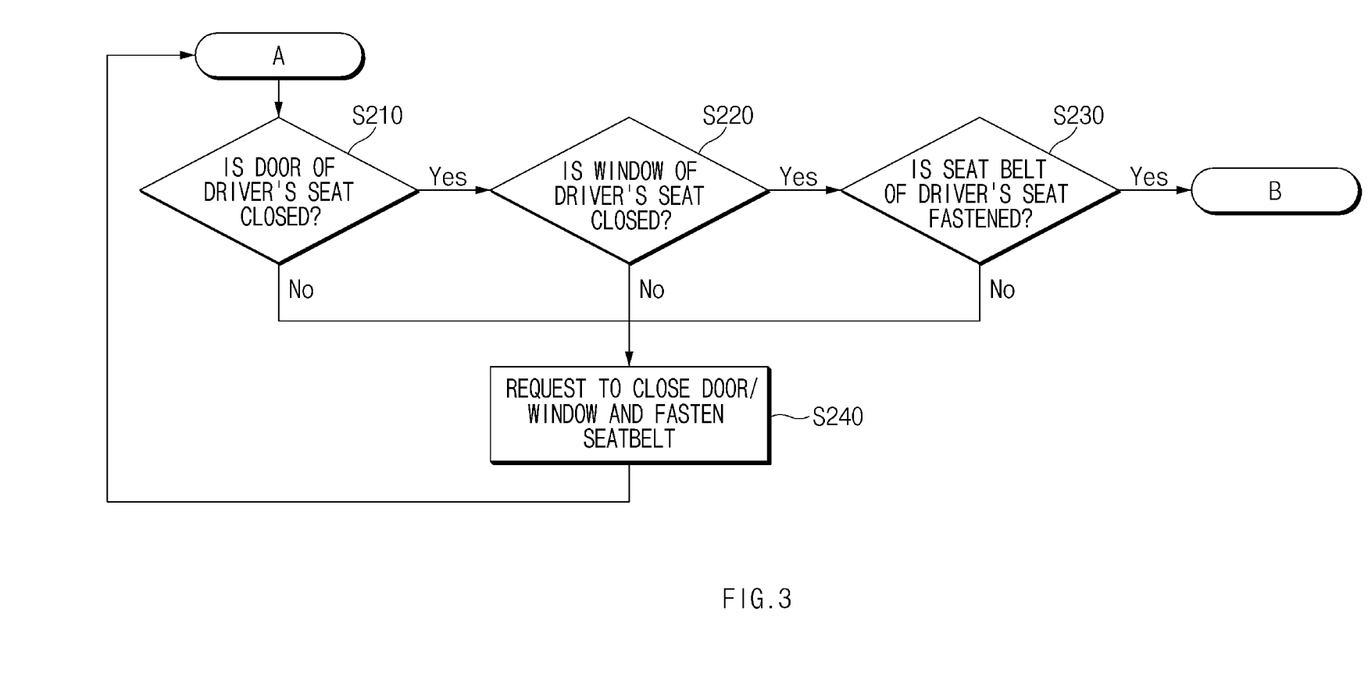
FIG. 3 is a flowchart illustrating a method for determining whether an exhalation component detection condition is satisfied, according to an exemplary embodiment of the present disclosure.

FIG. 3 is a flowchart illustrating a method for determining whether an exhalation component detection condition is satisfied, according to one exemplary embodiment of the present disclosure. As shown in FIG. 3, the controller 140 may be configured to determine whether the door at the driver's seat is closed based on the environment of the driver's seat detected by the sensor 120 (S210). In response to determining in S210 that the door at the driver's seat is closed (Y), the controller 140 may be configured to determine whether the window at the driver's seat is closed (S220). In response to determining in S220 that the window of the driver's seat is closed (Y), the controller 140 may be configured to determine whether the seat belt of the driver's seat is fastened (S230).

In response to determining in S230 that the seat belt of the driver's seat is fastened (Y), the controller 140 may be configured to determine that the condition for detecting the components of the exhalation of the passenger is satisfied. That is, when the door and the window at the driver's seat are closed to block the inflow of the air from the outside, to more easily detect the alcohol concentration in the exhalation of the passenger, and when the seat belt of the driver's seat is fastened, to determine that the passenger is seated on the driver's seat, the controller 140 may be configured to determine that the condition for detecting the components of the exhalation of the passenger is satisfied.

In response to determining that the door at the driver's seat is open (N) in S210, the window at the driver's seat is open (N) in S220, or the seat belt of the driver's seat is not fastened (N) in S230, the controller 140 may be configured to determine that the condition for detecting the components of the exhalation of the passenger is not satisfied. That is, when the door and the window at the driver's seat are opened, allowing the inflow of the air from the outside, and thus, it may be difficult to detect the alcohol concentration in the exhalation of the passenger, and when the seat belt of the driver's seat is not fastened, thus determining that the passenger is not seated on the driver's seat, the controller 140 may be configured to determine that the condition for detecting the components of the exhalation of the passenger is not satisfied. In addition, in response to determining that the condition for detecting the components of the exhalation of the passenger is not satisfied, the controller 140 may be configured to output the message informing the same through the display 130 (S240). In S240, the controller 140 may be configured to output the message of 'request to close the door/window and fasten the seat belt of the driver's seat' through the display 130.

Figure 4:
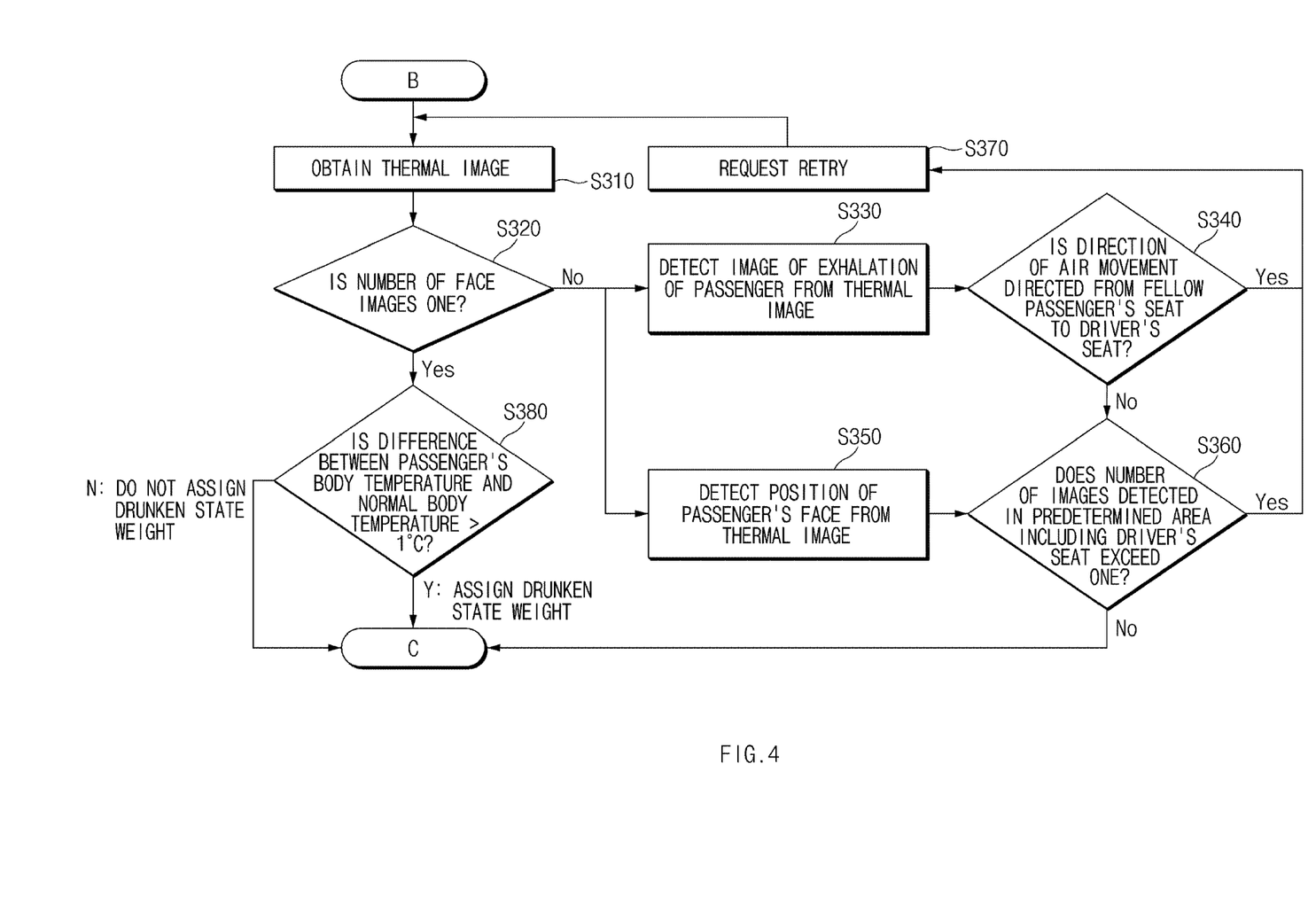
FIG. 4 is a flowchart illustrating a method for determining whether exhalation of a passenger is exhalation of a driver, according to an exemplary embodiment of the present disclosure.

FIG. 4 is a flowchart illustrating a method for determining whether exhalation of a passenger is exhalation of a driver, according to an exemplary embodiment of the present disclosure. As shown in FIG. 4, the controller 140 may be configured to obtain the thermal image for the face image of the passenger from the camera (e.g., the thermal camera) (S310). The controller 140 may be configured to detect the face image based on the thermal image obtained in S310, and determine whether the number of detected face images is one (S320). In response to determining in S320 that the number of face images is not one (N), the controller 140 may be configured to determine that the number of face images exceeds one.

In particular, the controller 140 may be configured to detect the image of the exhalation of the passenger based on the thermal image (S330). The controller 140 may also be configured to determine the direction of the air movement by the exhalation of the passenger based on the image of the exhalation of the passenger detected in S330, and then, determine whether the direction of the air movement is directed from the passenger's seat to the driver's seat (S340). In addition, the controller 140 may be configured to detect the position of the passenger's face based on the thermal image (S350), and determine whether the number of images detected in the predetermined area including the driver's seat exceeds one (S360).

In response to determining in S340 that the direction of the air movement is not directed from the passenger's seat to the driver's seat (N), and in response to determining in S360 that the number of face images detected in the predetermined area including the driver's seat does not exceed one (N), the controller 140 may be configured to determine the exhalation of the passenger as the exhalation of the driver. In other words, when the number of face images in the predetermined area including the driver's seat does not exceed one, the controller 140 may be configured to determine that only the passenger in the driver's seat is detected. Further, since the direction of the air movement is not directed from the passenger's seat to the driver's seat, the exhalation of the passenger in the driver's seat may be determined as the exhalation of the driver.

Furthermore, in response to determining in S340 that the direction of the air movement is directed from the passenger's seat to the driver's seat (Y), and in S360 that the number of face images detected in the predetermined area including the driver's seat exceeds one (Y), the controller 140 may not be configured to determine the exhalation of the passenger as the exhalation of the driver. In other words, when the number of face images in the predetermined area including the driver's seat exceeds one, the controller 140 may be configured to determine that the passenger is detected in addition to the driver in the driver's seat in the area adjacent to the driver's seat, and may not be configured to determine the exhalation of the passenger as the exhalation of the driver since the direction of the air movement is directed from the passenger's seat to the driver's seat. Further, the controller 140 may be configured to output the message providing a notification that the exhalation of the passenger is not determined as the exhalation of the driver through the display 130 (S370). The controller 140 may be configured to output the message that requests the retry of the exhalation operation through the display 130 to measure the exhalation of the passenger in S370, according to an exemplary embodiment.

In response to determining that the number of face images is one as the determination result of whether the number of face images in the thermal image is one in S320, the controller 140 may be configured to determine that the face image of the passenger is not detected. In other words, when the number of face images in the thermal image is one, the controller 140 may be configured to determine the passenger seated in the driver's seat as the driver, and thus may determine the exhalation of the passenger as the exhalation of the driver.

Figure 5:
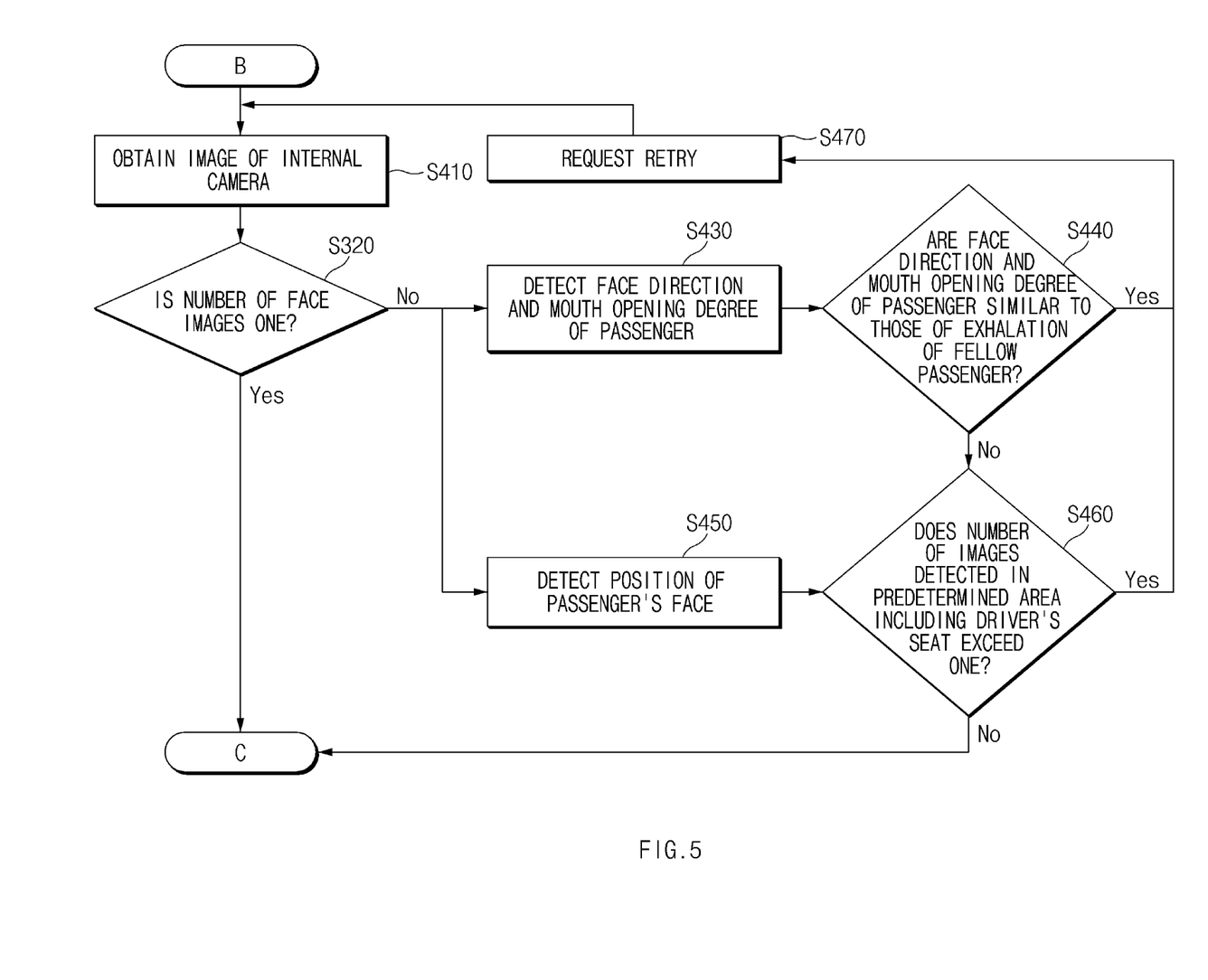
FIG. 5 is a flowchart illustrating a method for determining whether exhalation of a passenger is exhalation of a driver, according to an exemplary embodiment of the present disclosure.

In response to determining that the number of face images is one (Y) in S320, the controller 140 may additionally be configured to determine whether the difference between the passenger's body temperature and the normal body temperature exceeds the predetermined temperature based on the thermal image (S380). The controller 140 may be configured to perform S380 to assign the weight for determining the state of the passenger as the intoxicated state. When the difference between the passenger's body temperature and the normal body temperature exceeds the predetermined temperature (Y) in S380, the controller 140 may be configured to determine that the passenger's state is likely to be the intoxicated state. When the difference between the passenger's body temperature and the normal body temperature is less than the predetermined temperature (N) in S380, the controller 140 does not assign the weight for determining that the passenger is in the intoxicated state FIG. 5 is a flowchart illustrating a method for determining whether exhalation of a passenger is exhalation of a driver, according to another exemplary embodiment of the present disclosure. As shown in FIG. 5, according to another exemplary embodiment of the present disclosure, the controller 140 may be configured to obtain the face image of the passenger from the camera (e.g., the CCD camera or the CMOS camera) (S410). The controller 140 may be configured to detect the face image based on the image obtained in S410, and determine whether the number of detected face images is one (S420). In response to determining in S420 that the number of face images is not one (N), the controller 140 may be configured to determine that the number of face images exceeds one. In particular, the controller 140 may be configured to detect the face direction and the mouth opening degree of the passenger based on the image obtained in S410 (S430).

The controller 140 may be configured to determine whether the face direction and the mouth opening degree of the passenger detected in S430 are similar to those of the exhalation of the fellow passenger (S440). The determining, by the controller 140, of whether the face direction and mouth opening degree of the passenger are similar to those of the exhalation of the fellow passenger in S440 is understood as determining of whether the passenger's face is directed from the passenger's seat to the position where the sensor 120 is disposed and whether the degree of mouth opening is similar to the degree of mouth opening during the exhalation. In addition, the controller 140 may be configured to detect the position of the passenger's face based on the image obtained in S410 (S450), and determine whether the number of images detected in the predetermined area including the driver's seat exceeds one (S460).

In response to determining in S440 that the face direction and the mouth opening degree of the passenger are not similar to those of the exhalation of the passenger (N), and in S460 that the number of face images in the predetermined area including the driver's seat does not exceed one (N), the controller 140 may be configured to determine the exhalation of the passenger as the exhalation of the driver. In other words, when the number of face images in the predetermined area including the driver's seat does not exceed one, the controller 140 may be configured to determine that only the passenger in the driver's seat is detected. Further, since the face direction of the passenger is not directed to the position where the sensor 120 is disposed from the passenger's seat, the controller 140 may be configured to determine that the exhalation of the passenger as the exhalation of the driver.

Additionally, in response to determining in S440 that the face direction and the mouth opening degree of the passenger are similar to those of the exhalation of the passenger (Y), and in S460 that the number of face images in the predetermined area including the driver's seat exceeds one (Y), the controller 140 may be configured to not determine the exhalation of the passenger as the exhalation of the driver. In other words, when the number of face images in the predetermined area including the driver's seat exceeds one, the controller 140 may be configured to determine that the passenger is detected in addition to the driver on the driver's seat in the area adjacent to the driver's seat.

Since the face direction of the passenger is directed from the passenger's seat to the position where the sensor 120 is disposed, the controller 140 may be configured to not determine the exhalation of the passenger as the exhalation of the driver. Further, the controller 140 may be configured to output the message providing a notification that the exhalation of the passenger is not determined as the exhalation of the driver through the display 130 (S470). The controller 140 may be configured to output a message that requests the retry of the exhalation operation through the display 130 to measure the exhalation of the passenger in S470, according to an exemplary embodiment.

Figure 6:
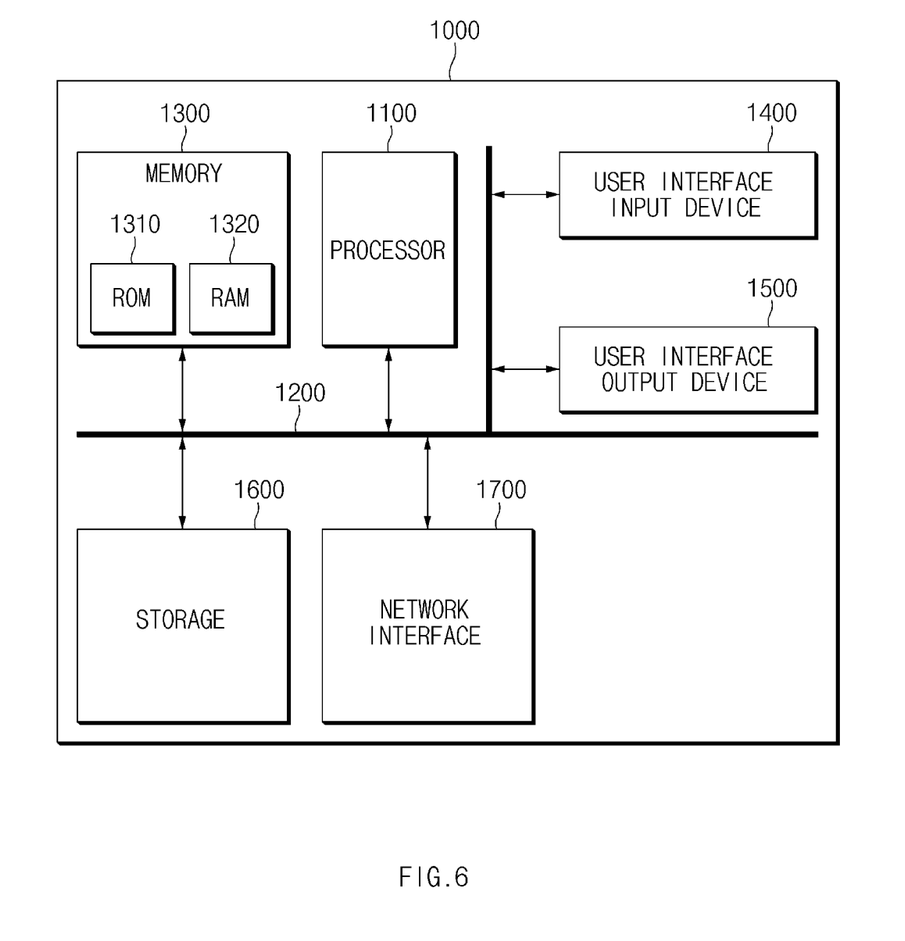
FIG. 6 is a diagram illustrating a configuration of a computing system that executes a method according to an exemplary embodiment of the present disclosure.

FIG. 6 illustrates a computing system in which a method according to an exemplary embodiment of the present disclosure is implemented. With reference to FIG. 6, a computing system 1000 may include at least one processor 1100, a memory 1300, a user interface input device 1400, a user interface output device 1500, storage 1600, and a network interface 1700 connected via a bus 1200.

The processor 1100 may be a central processing unit (CPU) or a semiconductor device that performs processing on commands stored in the memory 1300 and/or the storage 1600. The memory 1300 and the storage 1600 may include various types of volatile or non-volatile storage media. For example, the memory 1300 may include a ROM (Read Only Memory) 1310 and a RAM (Random Access Memory) 1320.

Thus, the operations of the method or the algorithm described in connection with the exemplary embodiments disclosed herein may be embodied directly in a hardware or a software module executed by the processor 1100, or in a combination thereof. The software module may reside on a storage medium (that is, the memory 1300 and/or the storage 1600) such as a RAM, a flash memory, a ROM, an EPROM, an EEPROM, a register, a hard disk, a removable disk, a CD-ROM. The exemplary storage medium is coupled to the processor 1100, which may read information from, and write information to, the storage medium. In another method, the storage medium may be integral with the processor 1100. The processor and the storage medium may reside within an application specific integrated circuit (ASIC). The ASIC may reside within the user terminal. In another method, the processor and the storage medium may reside as individual components in the user terminal.

The description above is merely illustrative of the technical idea of the present disclosure, and various modifications and changes may be made by those skilled in the art without departing from the essential characteristics of the present disclosure. Therefore, the exemplary embodiments disclosed in the present disclosure are not intended to limit the technical idea of the present disclosure but to illustrate the present disclosure, and the scope of the technical idea of the present disclosure is not limited by the embodiments. The scope of the present disclosure should be construed as being covered by the scope of the appended claims, and all technical ideas falling within the scope of the claims should be construed as being included in the scope of the present disclosure.

The apparatus and the method for controlling the alcohol interlock according to an exemplary embodiment of the present disclosure may prevent the abnormal measurement of the driver or the surrogate measurement of the fellow passenger, so that the driver's own blood alcohol concentration may be detected more accurately, and further the intoxicated driving may be fundamentally prevented.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An apparatus for controlling alcohol interlock, comprising:
a sensor configured to sense an environment of a driver's seat;
a camera configured to obtain a face image of a passenger and an image of exhalation of the passenger; and
a controller configured to:
activate a start lock mode of a vehicle and determine whether a condition for detecting components of the exhalation of the passenger is satisfied based on the environment of the driver's seat;
determine whether the exhalation of the passenger is exhalation of a driver based on the face image of the passenger and the image of the exhalation of the passenger; and
determine whether to detect alcohol concentration included in the exhalation of the passenger based on a determination result of the exhalation of the passenger.

2. The apparatus of claim 1, wherein the controller is configured to:
determine whether a door at the driver's seat is opened, whether a window at the driver's seat is opened, and whether a seat belt of the driver's seat is fastened based on the environment of the driver's seat; and
determine whether the condition for detecting the components of the exhalation is satisfied based on a determination result of the door, window, and seat belt.

3. The apparatus of claim 2, wherein the controller is configured to determine that the condition for detecting the components of the exhalation is satisfied in response to determining that the door is closed, the window is closed, and the seat belt of the driver's seat is fastened.

4. The apparatus of claim 1, wherein the camera includes a thermal imaging camera configured to detect thermal images of a passenger's face and the exhalation of the passenger.

5. The apparatus of claim 4, wherein the controller is configured to:
determine a number of face images detected based on the thermal image;
detect the image of the exhalation of the passenger based on the thermal image to determine a direction of air movement by the exhalation of the passenger;
detect a position of the passenger's face based on the thermal image to determine whether the number of face images in a predetermined area including the driver's seat exceeds one; and
determine whether the exhalation of the passenger is exhalation of the driver based on a determination result of the number of face images.

6. The apparatus of claim 5, wherein the controller is configured to determine the exhalation of the passenger as the exhalation of the driver when the number of face images detected based on the thermal image exceeds one, the direction of the air movement is not directed from a passenger's seat to the driver's seat, and the number of face images in the predetermined area including the driver's seat does not exceed one.

7. The apparatus of claim 6, wherein the controller is configured to determine the exhalation of the passenger as the exhalation of the driver in response to determining that the number of face images detected based on the thermal image is one.

8. The apparatus of claim 7, wherein the controller is configured to, when the exhalation of the passenger is determined as the exhalation of the driver, determine whether to detect the alcohol concentration in the exhalation of the passenger detected as the exhalation of the driver.

9. The apparatus of claim 8, wherein the controller is configured to release the start lock mode when the alcohol concentration is less than a reference value.

10. The apparatus of claim 4, wherein the controller is configured to:
determine a number of detected face images, a direction of the passenger's face, and a degree of mouth opening based on the face image of the passenger; and
determine whether the exhalation of the passenger is the exhalation of the driver based on a determination result of the number of detected face images, the direction of the passenger's face, and the mouth opening degree.

11. A method for controlling alcohol interlock, comprising:
sensing, by a controller, an environment of a driver's seat;
obtaining, by the controller, a face image of a passenger and an image of exhalation of the passenger;
activating, by the controller, a start lock mode of a vehicle and determining whether a condition for detecting components of the exhalation of the passenger is satisfied based on the environment of the driver's seat;
determining, by the controller, whether the exhalation of the passenger is exhalation of a driver based on the face image of the passenger and the image of the exhalation of the passenger; and
determining, by the controller, whether to detect alcohol concentration in the exhalation of the passenger based on a determination result of the exhalation of the passenger.

12. The method of claim 11, wherein the determining of whether the condition for detecting the components of the exhalation of the passenger is satisfied includes:
determining, by the controller, whether a door at the driver's seat is opened, whether a window at the driver's seat is opened, and whether a seat belt of the driver's seat is fastened based on the environment of the driver's seat; and
determining, by the controller, whether the condition for detecting the components of the exhalation is satisfied based on a determination result of the door, the window, and the seat belt.

13. The method of claim 12, wherein the determining of whether the condition for detecting the components of the exhalation of the passenger is satisfied includes:
determining, by the controller, that the condition for detecting the components of the exhalation is satisfied in response to determining that the door is closed, the window is closed, and the seat belt of the driver's seat is fastened.

14. The method of claim 11, wherein the obtaining of the face image of the passenger and the image of the exhalation of the passenger includes;
obtaining, by the controller, thermal images of a passenger's face and the exhalation of the passenger.

15. The method of claim 14, wherein the determining of whether the exhalation of the passenger is the exhalation of the driver includes:
determining, by the controller, a number of face images detected based on the thermal image;
detecting, by the controller, the image of the exhalation of the passenger based on the thermal image to determine a direction of air movement by the exhalation of the passenger;
detecting, by the controller, a position of the passenger's face based on the thermal image to determine whether the number of face images in a predetermined area including the driver's seat exceeds one; and
determining, by the controller, whether the exhalation of the passenger is exhalation of the driver based on a determination result of the number of face images.

16. The method of claim 15, wherein the determining of whether the exhalation of the passenger is the exhalation of the driver includes:
determining, by the controller, the exhalation of the passenger as the exhalation of the driver when the number of face images detected based on the thermal image exceeds one, the direction of the air movement is not directed from a passenger's seat to the driver's seat, and the number of face images in the predetermined area including the driver's seat does not exceed one.

17. The method of claim 16, wherein the determining of whether the exhalation of the passenger is the exhalation of the driver includes:

determining, by the controller, the exhalation of the passenger as the exhalation of the driver in response to determining that the number of face images detected based on the thermal image is one.

18. The method of claim 17, wherein the determining of whether to detect the alcohol concentration in the exhalation of the passenger based on the determination result includes:

in response to determining that the exhalation of the passenger is determined as the exhalation of the driver, determining, by the controller, whether to detect the alcohol concentration in the exhalation of the passenger detected as the exhalation of the driver.

19. The method of claim 18, further comprising:

releasing, by the controller, the start lock mode when the alcohol concentration is less than a reference value.

20. The method of claim 14, wherein the determining of whether the exhalation of the passenger is the exhalation of the driver includes:

determining, by the controller, a number of detected face images, a direction of the passenger's face, and a degree of mouth opening based on the face image of the passenger; and determining, by the controller, whether the exhalation of the passenger is the exhalation of the driver based on a determination result of the number of detected face images, the direction of the passenger's face, and the mouth opening degree.

* * * * *